United States Patent [19]

Ison

[11] Patent Number: Plant 7,296

[45] Date of Patent: Aug. 14, 1990

[54] FRY SEEDLESS

[76] Inventor: William G. Ison, Rte. 1, Box 19, Hwy. 19, Brooks, Ga. 30205

[21] Appl. No.: 166,253

[22] Filed: Mar. 10, 1988

[51] Int. Cl.[5] ..... A01H 5/00

[52] U.S. Cl. ..... Plt./47

[58] Field of Search ..... Plt./47

*Primary Examiner*—Robert E. Bagwill

*Attorney, Agent, or Firm*—Eugene T. Holmes

[57] ABSTRACT

A cross between the female variety Farrer and the pollen parent variety Redgate to produce an improved variety of muscadine grape.

1 Drawing Sheet

DESCRIPTION OF THE VARIETY

A cross between the female variety Farrer and the pollen parent Redgate, Farrer being 20% to 30% seedless.

The primary objective of the breeding was to produce an improved variety of muscadine grape; the fruit to have superior characteristics for fresh fruit than either of its parents. These characteristics include breeding for seedless varieties, high quality, 100% dry scar for longer shelf life for fresh fruit, high sugar content, and the plant to be disease free, vigorous and productive.

The new variety is similar in size to the pollen parent. The new variety resembles in color the pollen parent. The fruit of this new variety contains an average of 20% soluble solids, which sugar content is comparable to the sugar content of the fruit of the female parent. The present variety yields on the average of ½ to four tons per acre in tests conducted at Ison's Nursery & Vineyards, Brooks, Ga.

Asexual reproduction of the new variety either by soft-wood cuttings or by layering as performed at Brooks, Ga. shows that the foregoing characteristics and distinctions come true to form and are established and transmitted through succeeding propagations.

The accompanying photograph shows a typical specimen of the vegetative growth and fruit of the new variety when the fruit is ripe and ready for picking and as true in color as is reasonably possible to make the same in color illustration of the characters.

The following is a detailed description of the new variety:

Species: *Vitis rotundifolia.*

Type: Vine.

Seed parent: Farrer, which is 20 to 30% seedless.

Parent pollen: Redgate.

Propagation: Holds its characteristics through succeeding propagation by either layering or by soft-wood cuttings.

Locality where grown: Brooks, Ga.

Fruit borne: In clusters of approximately 5 to 28 berries per cluster.

Fruit size: Small to Medium, ¼" to ¾" in diameter.

Fruit color: Greyed Orange Group 176A, Fan 4 of the Royal Horticultural Society, London, England.

Sugar content: Average 20% soluble solids.

Skin: Thin.

Fruit shape: Round.

Pulp: A. Color group Fan 195B, Fan 4 Royal Horticultural Society, London, England. B. Pulp, melty, soft and juicy consistency when compared to most muscadine varieties.

Reproductive organs: Self-infertile.

Growth habits: Vine vigorous, requires support. Low to good, erratic production.

Canes: Medium.

Maturity date: Usually ripens about October 5 at Brooks, Ga.

Diseases: Tolerant to diseases.

This description was made from a muscadine vine grown at Ison's Nursery & Vineyards, Brooks, Ga. 30205.

I claim:

1. The new and distinct variety of grape plant as described and illustrated.

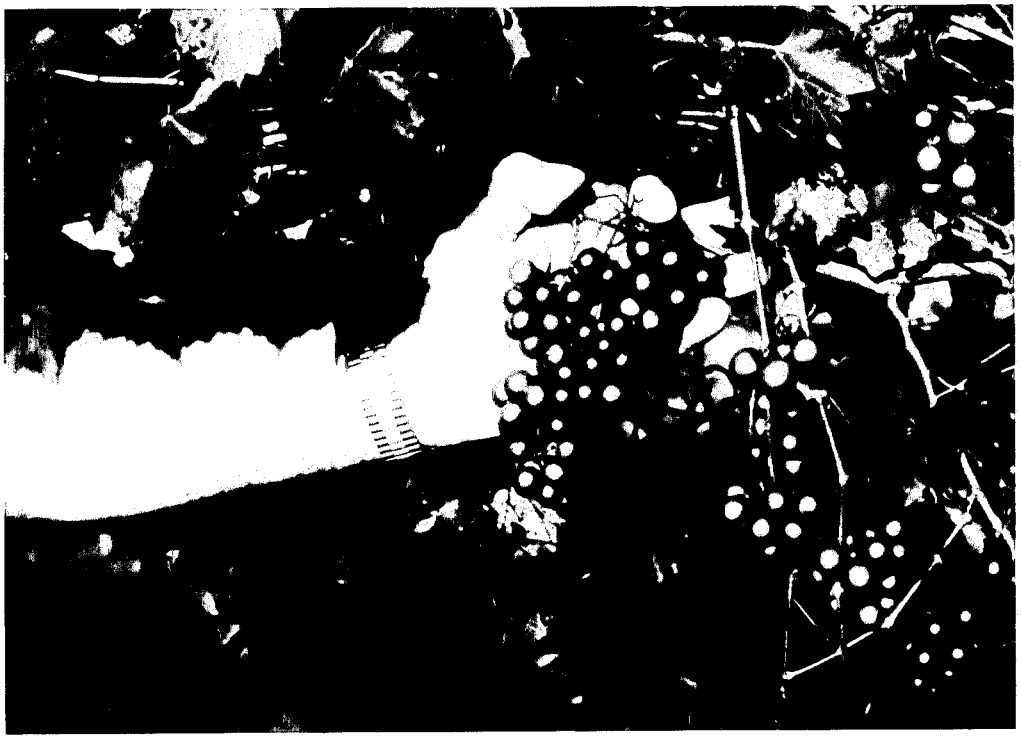

* * * * *